United States Patent [19]

Schaafsma et al.

[11] 4,012,418
[45] Mar. 15, 1977

[54] PROCESS FOR THE PREPARATION OF PYRROLIDONE-2

[75] Inventors: Sijbrandus E. Schaafsma, Beek; Leonardus H. Geurts, Sittard, both of Netherlands

[73] Assignee: Stamicarbon B.V., Geleen, Netherlands

[22] Filed: Sept. 23, 1975

[21] Appl. No.: 616,011

[30] Foreign Application Priority Data

Sept. 26, 1974 Netherlands ............... 7412694

[52] U.S. Cl. ............. 260/326.5 FN; 260/326.5 FL; 260/326.62; 260/326.9
[51] Int. Cl.$^2$ .................................. C07D 207/26
[58] Field of Search .......... 260/326.5 FN, 326.5 FL

[56] References Cited

OTHER PUBLICATIONS

King et al., J. Chem. Soc., pp. 4268–4271 (1952).
Buckley et al., J. Chem. Soc. pp. 1508–1511 (1947).
Beicke et al., J. Org. Chemistry; vol. 26 pp. 1826–1831 (1961).

Primary Examiner—Donald G. Daus
Assistant Examiner—Mary C. Vaughn
Attorney, Agent, or Firm—Cushman, Darby & Cushman

[57] ABSTRACT

Pyrrolidone-2, or N-substituted derivatives thereof, is prepared by heating an aqueous solution of the corresponding 2-amino-$\Delta^1$-pyrroline at a temperature of 90°–290° C. The process does not require the use of a Raney nickel catalyst and produces the pyrrolidone-2 product in substantial yields.

6 Claims, No Drawings

PROCESS FOR THE PREPARATION OF PYRROLIDONE-2

This invention relates to a process for the preparation of pyrrolidone-2 optionally N-substituted, by water-treatment of a 2-amino-Δ¹-pyrroline, which as used herein also denotes the tautomeric 2-imino-pyrrolidine form.

It is well known as described in the Journal of the Chemical Society 1947, pages 1508–1511 and Journal of Organic Chemistry 1961, page 1830 that hydrolysis of such a pyrroline compound can be effected by boiling the compound to be hydrolyzed with water in the presence of Raney nickel under reflux conditions. However, the yield obtained by this method is unsatisfactory. According to another well-known method as described in the Journal of the Chemical Society 1952, pages 4268–4271 such a hydrolysis reaction is carried out at 80°–83° C. with diluted hydrochloric acid in a solution that also contains sodium nitrite. However, the yield using this reaction is even lower than in the former method.

We have now found and describe below a process in which the hydrolysis of a 2-amino-Δ¹-pyrroline can be effected with a considerably higher yield and without the use of Raney nickel or other auxiliary substances.

The process according to the present invention for the preparation of a pyrrolidone-2 by hydrolyzing a 2-amino-Δ¹-pyrroline, together with the water, is heated for a period of time at a temperature of 90°–290° C.

As the temperature according to the process of the invention is higher, a shorter heating period is sufficient. If a temperature of 210° C. is used for instance, a virtually quantitative yield is possible in about 2 hours. For practical purposes, a temperature of 140°–240° C is most suitable and hence is preferred.

The time required to complete the reaction is dependent upon such factors as temperature and to a lesser extent, pressure. Determination of the completion of the reaction is accomplished by conventional means but generally the reaction times will vary between about 1 and about 5 hours.

The pressure at which the reaction is conducted as such is not critical but should necessarily be sufficient such that the water is in the liquid state at the temperature at which the reaction is conducted.

The reaction is preferably conducted in a sealed chamber or vessel, or in the presence of an inert atmosphere such as nitrogen or the like. As it is convenient to commence from an aqueous solution of the starting materials a molar excess of water is necessarily present.

The amino-pyrrolines that can be used as starting materials according to the invention may optionally be N-substituted The substituents may be $C_1$–$C_4$ alkyl groups or $C_1$–$C_3$ alkylcyanogroups. Examples of suitable substituted starting materials, are N-alkyl-2-imino-pyrrolidines and N-N'-dialkyl-2-imino-pyrrolidines. A preferred starting product is the compound 2-(N-γ-cyano-propyl)amino-Δ¹-pyrroline. This compound has not been described in literature so far and can be prepared by heating γ-aminobutyronitrile, as described in a patent application Ser. No. 616,012, filed simultaneously with the present application; the entire disclosure of that application is incorporated herein by reference. If this new compound is subjected to the hydrolysis treatment according to the invention, a gross reaction is effected in which two moles of pyrrolidone-2 are formed for every mole of 2-(N-γ-cyanopropyl)-amino-Δ¹-pyrroline. Pyrrolidone-2 is useful as a starting material for the preparation of nylon-4, as described in U.S. Pat. No. 2,638,463.

The process according to the present invention will be further elucidated in the following illustrated examples. Unless otherwise indicated all parts and percentages are by weight.

EXAMPLE 1

A mixture of 84.0 g (1 mole) of 2-amino-Δ¹-pyrroline and 330 g of water was heated at 210° C for 2 hours in a closed autoclave with a capacity of 0.5 liter. Upon cooling to room temperature, the reaction mixture was analyzed gas-chromatochraphically. No other compound could be detected besides ammonia and pyrrolidone.

Quantitative analysis showed that the reaction mixture contained 84.0 g of pyrrolidone-2, which was 99% of the theoretically possible amount.

Distillation of the reaction mixture at 124° C and 10 mm Hg gave 78.3 g of product which contained over 99% of pyrrolidone-2 according to analysis.

EXAMPLE 2

A mixture of 15.1 g (0.1 mole) of 2-(N-γ-cyanopropyl)amino-66 ¹-pyrroline and 35 g of water was heated at 210° C. for 2 hours in a closed steel tube. Upon cooling to room temperature the reaction mixture was analyzed gas-chromatographically.

The reaction mixture contained 16.2 g of pyrrolidone-2, which corresponded to a yield of 95.5%.

The starting product was prepared as follows:

84 g (1 mole) of γ-aminobutyronitrile was heated to 100° C. under a nitrogen atmosphere in a flask provided with a stirrer. The reaction mixture was kept at this temperature for 4 hours, after which the development of ammonia that occurred during the heating was complete. The reaction mixture was cooled to room temperature and the liquid was then distilled at reduced pressure. Two fractions were separated off:

Fraction 1 : 25.2 g of product were obtained at 95°–100° C and 4 mm Hg.
Fraction II: 45.3 g of product were obtained at 113°–120° C and 0.3 mm Hg.
Fraction II was distilled again, when 40.8 g (yield 54%) of product were obtained which solidified upon cooling. The melting point of this product was 30°–32° C. The following structure was determined by means of mass spectrometry, nuclear spin resonance, and infra-red spectrometry:

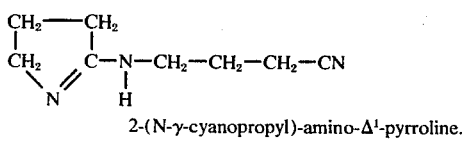

2-(N-γ-cyanopropyl)-amino-Δ¹-pyrroline.

EXAMPLE 3

A mixture of 15.1 g (1 mole) of 2-(N-γ-cyanopropyl) amino-Δ¹-pyrroline and 25 g of water was heated at 155° C for 4 hours in a closed steel tube. Upon cooling to room temperature, the reaction mixture was analyzed gas-chromatographically.

According to the analysis, the reaction mixture contained 16.8 g of pyrrolidone-2, the yield being 99%.

EXAMPLE 4

A mixture of 10 g of 2-amino-$\Delta^1$-pyrroline and 90g of water was heated at 100° C for 7 hours in a closed steel tube. Upon cooling to room temperature, the reaction mixture was analyzed gas-chromatographically.

The reaction mixture contained 96% of pyrrolidone-2 (yield 95%).

EXAMPLE 5

A mixture consisting of 53% of N-methyl-2-iminopyrrolidine and 47% of N,N'-dimethyl-2-iminopyrrolidine (prepared according to the method described in J. Org. Chem. 32 pages 738–740), together with 90 g of water, was heated at 210° C for 2 hours in a closed steel tube. Upon cooling to room temperature, the reaction mixture was analyzed gas-chromatographically.

The reaction mixture contained 13.4 g of N-methyl-pyrrolidone-2, which corresponded to a yield of 94%.

What is claimed is:

1. A process for the preparation of a pyrrolidone-2 compound of the formula:

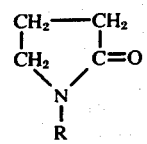

wherein R is hydrogen or $C_1 - C_4$ alkyl, consisting of heating an aqueous solution of a 2-amino-$\Delta^1$-pyrroline of the formula:

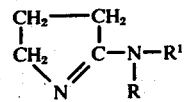

or the tautomeric 2-imino-pyrrolidine, wherein R is hydrogen or, when using the tautomeric 2-imino-pyrrolidine, R is hydrogen or a $C_1 - C_4$ alkyl group, and $R^1$ is hydrogen, a $C_1 - C_4$ alkyl group or a $C_1 - C_3$ alkyl-cyano group, by heating at a temperature of 90° – 290° C.

2. The process of claim 1 wherein an aqueous solution of 2-(N-$\gamma$-cyanopropyl)-amino-$\Delta^1$-pyrroline is heated.

3. The process of claim 1 wherein an aqueous solution of 2-amino-$\Delta^1$-pyrroline is heated.

4. The process of claim 1 wherein an aqueous solution of N-methyl-2-iminopyrrolidine is heated.

5. The process of claim 1 wherein an aqueous solution of N,N'-dimethyl-2-iminopyrrolidine is heated.

6. The process of claim 1 wherein the heating is effected at a temperature of 140° – 240° C.

* * * * *